United States Patent
Lightcap et al.

(10) Patent No.: US 7,560,033 B2
(45) Date of Patent: Jul. 14, 2009

(54) MULTI-FUNCTIONAL OXIDIZING COMPOSITION

(75) Inventors: Edward Blake Lightcap, Landenberg, PA (US); Michael Brian Coxey, Norristown, PA (US); Thomas Peter Tufano, Wilmington, DE (US)

(73) Assignee: E.I. duPont de Nemours and Company

( * ) Notice: Subject to any disclaimer, the term of this patent is extended or adjusted under 35 U.S.C. 154(b) by 71 days.

(21) Appl. No.: 10/963,932

(22) Filed: Oct. 13, 2004

(65) Prior Publication Data

US 2006/0078584 A1   Apr. 13, 2006

(51) Int. Cl.
C02F 1/68    (2006.01)
C02F 1/76    (2006.01)
C02F 1/72    (2006.01)

(52) U.S. Cl. .................. 210/749; 210/753; 210/754; 210/755; 210/756; 210/758; 210/759

(58) Field of Classification Search .............. 210/749, 210/753–756, 758, 759
See application file for complete search history.

(56) References Cited

U.S. PATENT DOCUMENTS

| | | | |
|---|---|---|---|
| 3,371,034 A | 2/1968 | Richards | |
| 3,671,629 A * | 6/1972 | Levy et al. ........... | 424/680 |
| 3,702,298 A | 11/1972 | Zsoldos et al. | |
| 3,939,072 A | 2/1976 | LaForte | |
| 4,594,091 A | 6/1986 | Girvan | |
| 4,725,437 A | 2/1988 | Kuhne | |
| 4,863,445 A | 9/1989 | Mayhan et al. | |
| 4,880,547 A * | 11/1989 | Etani ................. | 210/728 |
| 4,975,109 A | 12/1990 | Friedman et al. | |
| 5,015,643 A | 5/1991 | Jones et al. | |
| 5,024,769 A | 6/1991 | Gallup | |
| 5,028,340 A | 7/1991 | Gallup | |
| 5,057,612 A | 10/1991 | Worley et al. | |
| 5,078,902 A | 1/1992 | Antelman | |
| 5,098,582 A | 3/1992 | Antelman | |
| 5,106,559 A | 4/1992 | Wiedrich et al. | |
| 5,130,033 A | 7/1992 | Thornhill | |
| 5,254,526 A | 10/1993 | Hamilton | |
| 5,256,182 A | 10/1993 | Friedman et al. | |
| 5,258,409 A | 11/1993 | Gay | |
| 5,338,461 A | 8/1994 | Jones | |
| 5,368,749 A | 11/1994 | Zonby | |
| 5,373,025 A | 12/1994 | Gay | |
| 5,476,670 A | 12/1995 | Hight et al. | |
| 5,478,482 A | 12/1995 | Jones et al. | |
| 5,490,983 A | 2/1996 | Worley et al. | |
| 5,501,802 A | 3/1996 | Thorp et al. | |
| 5,514,287 A | 5/1996 | Jones et al. | |
| 5,670,646 A | 9/1997 | Worley et al. | |
| 5,700,377 A | 12/1997 | Cox | |
| 5,779,913 A | 7/1998 | Denkewicz, Jr. et al. | |
| 5,849,985 A | 12/1998 | Tieckelmann et al. | |
| 5,858,246 A | 1/1999 | Rafter et al. | |
| 5,877,389 A | 3/1999 | Sorokin et al. | |
| 5,882,526 A | 3/1999 | Brown et al. | |
| 5,902,818 A | 5/1999 | Worley et al. | |
| 6,110,387 A | 8/2000 | Choudhury et al. | |
| 6,149,819 A | 11/2000 | Martin et al. | |
| 6,180,412 B1 | 1/2001 | Kroll | |
| 6,207,048 B1 | 3/2001 | Bonelli | |
| 6,255,117 B1 | 7/2001 | Johnson | |
| 6,303,038 B1 | 10/2001 | Sanders et al. | |
| 6,409,926 B1 | 6/2002 | Martin | |
| 6,727,219 B2 | 4/2004 | Buckland et al. | |
| 2003/0080317 A1 | 5/2003 | Speronello et al. | |
| 2004/0002433 A1 * | 1/2004 | Buckland et al. ....... | 510/302 |
| 2005/0035065 A1 | 2/2005 | Martin | |

FOREIGN PATENT DOCUMENTS

| | | |
|---|---|---|
| DE | 19646225 | 5/1998 |
| EP | 0 481 269 B1 | 4/1992 |
| EP | 0 832 852 A2 | 4/1998 |
| EP | 0 844 215 A2 | 5/1998 |
| GB | 1 433 606 | 4/1976 |
| GB | 1 483 501 | 8/1977 |
| JP | 59001599 A | 7/1984 |
| JP | 59212414 A | 9/1993 |
| JP | 1994121991 A | 5/1994 |
| JP | 1999019663 A | 1/1999 |
| LT | 4490 B | 4/1999 |
| WO | WO 89/12606 | 12/1989 |

(Continued)

OTHER PUBLICATIONS

DuPont Specialty Chemicals, Dupont Oxone® monopersulfate compound, Technical Information Bulletin No. 290836D, Feb. 1998, pp. 1-8, Wilmington, Delaware.

(Continued)

*Primary Examiner*—Sreeni Padmanabhan
*Assistant Examiner*—Renee Claytor
(74) *Attorney, Agent, or Firm*—Anthony Chi

(57) ABSTRACT

A composition comprising a stable anhydrous mixture of an oxidizing agent and an active halogen agent wherein the oxidizing agent is potassium hydrogen peroxymonosulfate and the active halogen agent is an alkali metal salt of dichloro-s-triazinetrione, halogenated dimethylhydantoin, or mixtures thereof, and a method of treating water with such compositions are disclosed.

6 Claims, No Drawings

FOREIGN PATENT DOCUMENTS

| | | |
|---|---|---|
| WO | WO 96/14092 | 5/1996 |
| WO | WO 97/34835 | 9/1997 |
| WO | WO 98/53679 | 12/1998 |
| WO | WO 99/59924 | 11/1999 |
| WO | WO 00/69778 | 11/2000 |
| ZA | 9701266 A | 2/1998 |

OTHER PUBLICATIONS

George P. Anipsitakis et al., Degradation of organic contaminants in water and wastewater with transition metal-catalyzed chemical oxidation, Department of Civil and Environmental Engineering, University of Cincinnati, Cincinnati, OH, 45221, USA, American Chemical Society, Division of Environmental Chemistry, 2002, 42(1), 48-51.

Eugen G. Leuze Verlag, Wet oxidation processes for wastewater treatment, General Review Journal, Galvanotechnik (1996), 87(10), 3392-3396.

V. F. Fedorko et al., Removal unsaturated organic compounds from wastewater, Commerical-Economical Inst., Lvov, Ukraine, Khimiya I Tekhnologiya Vodyl, 1993, 15(9-10), 651-2.

Hussain Al-Ekabi et al., Titanium dioxide advanced photo-oxidation technology: effect of electron acceptors, Nutech Environ., Nutech Energy Syst. Inc., London, ON, N5W 4C8, Can., Trace Metals in the Environment (1993), 3(Photocatalytic Purification and Treatment of Water and Air), 321-35.

B. Meunier, Oxidation of chlorine-containing pollutants catalyzed by biomimetic catalysts, Journal Recents Progres en Genie des Procedes (1992), 6(20, Technol. Innovantes Epur. Eaux), 203-5.

Karl Heinz Gregor, Cyanide detoxification with peroxygens, Period-Chem. GmbH, Hoellriegelskreuth, D-8023, Germany, General Review Conference, Chem. Oxid., Proc. Int. Symp., 1st(1992), Meeting Date 1991, 98-103. Publisher: Technomic, Lancaster, PA, USA.

Anastassia Kotronarou et al., Peroxymonosulfate: an alternative to hydrogen peroxide for the control of hydrogen sulfide, Research Journal of the Water Pollution Control Federation (1991), 63(7), 965-70.

Anonymous, Detoxification of cyanide-containing wastewater with monopersulfate, Fed. Rep. Ger., Chemie Technik (Heidelberg, Germany) (1998), 17(8), 18.

Milton Roth et al, Evaluation of the ultraviolet-ozone and ultraviolet-oxidant treatment of pink water, Large Caliber Weapon Syst. Lab., Army Armament Res. Dev. Command, Dover, NJ, USA, Report (1979, EPA/600/2-79/129; Order No. PB-300763, 41 pp. Avail.: NTIS from: Gov. Rep. Announce. Index (U.S.) 1979, 79(26), 254.

Claude Henry et al., Decyaniding with peroxidized products. Theory and practice of purification of waste water containing cyanide compounds from the mineral and organic industries, Inst. Rech. Hydrol., Nancy, Fr., General Review Journal, Trib. CEBEDEAU (Cent. Belge Etude Doc. Eaux) (1971), 24(331-332), 282-94.

Inge Van Kemenade et al., Bioremediation enhancement of phenanthrene contaminated soils by chemical pre-oxidation, Dep. Chem. Eng., Univ. Waterloo, Waterloo, ON, N2L 3G1, Can., Journal Hazardous Waste & Hazardous Materials (1995), 12(4), 345-55.

Alexander Sorokin et al. Efficient $H_2O_2$ oxidation of chlorindated phenols catalyzed by supported iron phthalocyanines, Laboratoire de Chimie de Coordination, CNRS, Toulouse, 31007, France, Journal of the Chemical Society, Chemical Communications (1994), (15), 1799-800.

Hans Schwarzer, Prevention of organohalogen-containing wastewater and liquid wastes by replacing hypochlorite by hydrogen peroxide in cyanide detoxification, Peroxid-Chemie G.m.b.H., Hoellriegelskreuth, 8023, Germany, Stuttgarter Berichte zur Abfallwirtschaft (1990), 39(Sonderabfallvermeidung), 173-89.

Eric A. Betterton, et al., Oxidation of aqueous hydrogen sulfide by peroxymonosulfate, University Arizona, Tucson, AZ, USA, Proceedings, Annual Meeting—Air & Waste Management Association (1989), $82^{nd}$(vol. 6), 89/93.5, 6 pp.

Derek W. Anderson, et al., Detoxification of HD using reactive powder systems, DERA, CBD Porton Down, Salisbury, Wiltshire, SP4 0JQ, UK, Proceedings of the ERDEC Scientific Conference on Chemical and Biological Defense Research, Aberdeen Proving Ground, MD, Nov. 18-21, 1997 (1998), Meeting Date 1997, 359-365. Editor(s): Berg, Dorothy A. Publisher: National Technical Information Service, Springfield, VA, USA.

* cited by examiner

MULTI-FUNCTIONAL OXIDIZING COMPOSITION

FIELD OF THE INVENTION

This invention relates to a solid composition comprising potassium monopersulfate and an active halogen agent, providing the dual functions of peroxygen oxidation and the establishment or maintenance of a free halogen residual, useful in the treatment of recirculating water systems such as in recreational, ornamental and industrial water applications.

BACKGROUND OF THE INVENTION

Trademarks are hereinafter shown in upper case.

The name "potassium monopersulfate" is commonly used in the trade, and is used hereinafter to refer to the mixed triple salt $2KHSO_5 \cdot KHSO_4 \cdot K_2SO_4$, a crystalline salt of enhanced solid-state stability. In the treatment of recirculating water systems, especially in swimming pools, spas and hot tubs, potassium monopersulfate is an effective non-chlorine oxidizer for the reduction of non-microbial, organic contaminants which make water dull and cloudy and reduce chlorine sanitizer efficiency. Various active halogen agents which dissolve in water to provide free available halogen are well-known in the art and are used as sanitizing agents to control microbial and algal growth in recirculating water systems.

Martin, in U.S. Pat. No. 6,409,926, uses the separate addition of a halogen donor source (including sodium dichloroisocyanurate), a coagulating agent, and a peroxygen compound (including potassium monopersulfate) for the removal of volatile halogenated compounds from the air and water in an indoor aquatic facility. Martin does not describe compositions comprising premixed potassium monopersulfate and an active halogen agent.

In general, commercial suppliers strongly recommend that chemicals providing a source of active oxygen should not be mixed with active halogen sources or precursors thereof. Many such mixtures are chemically unstable as solid mixtures, and are capable of exothermic reactions with the evolution of poisonous halogen gas. For example, the following recommendations are made:

The MSDS of PPG for Calcium Hypochlorite Granular (Date Jun. 15, 1998) states:

"DANGER! Strong Oxidizing Agent! Mix only with water. Contamination may cause fire or explosion. Do not add this product to any dispensing device containing remnants of any other product" [emphasis added].

The Clinfax MSDS for CLINIFAX Bleach Tablets (sodium dichloro-s-triazinetrione dihydrate, date July 1998) states:

"Substances to be avoided (incompatible substances): Organic substances, oils, fat, saw dust, reducing agents, nitrogen-containing compounds, sodium hypochlorite, calcium hypochlorite, other oxidizing agents, acids and alkaline substances" [emphasis added].

The MSDS of the U.S. Department of Transportation, 49 CFR, for Microphor Chlorinating Slugs (trichloroisocyanuric acid), Revised Jun. 22, 2000 states:

"Incompatibility: Organic materials, reducing agents, nitrogen-containing materials, other oxidizers, acids, bases, oils, grease, sawdust, dry fire extinguishers containing monoammonium compounds" [emphasis added].

The OXONE monopersulfate compound technical information bulletin P-200838 (4/2000), from E. I. du Pont de Nemours and Company, lists the following materials as "incompatible" and which should not be transported or stored in proximity to OXONE:

"Compounds containing halides or active halogens. OXONE can oxidize halides to active halogens (for example chloride to chlorine), and the acidity of OXONE might react with an active halogen compound to release halogen gas"

Generally, if potassium monopersulfate is combined with alkali and alkaline earth hypochlorites, the mixture is not stable. Such mixtures are unsafe for the end-user because, when contacted with water, poisonous chlorine gas is evolved immediately due to the acidic nature of potassium monopersulfate and the high solubility and reactivity of the hypochlorite salt in water. Furthermore, such mixtures are not stable because the reactivity of hypochlorite salts and potassium monopersulfate is very exothermic and can cause fires or explosions.

It is therefore desirable to have a safe, stable combination of potassium monopersulfate with an active halogen agent in a single composition that provides the dual action of peroxygen oxidation and the establishment or maintenance of a free halogen residual to control microbial and algal growth. Such a composition would be useful in the treatment of recirculating water systems, such as in various types of recreational, ornamental and industrial water systems. The present invention provides safe and stable compositions which comprise mixtures of potassium monopersulfate and suitable active halogen agents.

SUMMARY OF THE INVENTION

The present invention comprises a composition comprising a stable anhydrous mixture of an oxidizing agent and an active halogen agent wherein the oxidizing agent is potassium monopersulfate and the active halogen agent is an alkali metal salt of dichloro-s-triazinetrione, halogenated dimethylhydantoin, or mixtures thereof.

The present invention further comprises a method of treating water comprising contacting the water with a composition comprising a stable anhydrous mixture of an oxidizing agent and an active halogen agent wherein the oxidizing agent is potassium monopersulfate and the active halogen agent is an alkali metal salt of dichloro-s-triazinetrione, halogenated dimethylhydantoin, or mixtures thereof.

The present invention further comprises a method to inhibit algae growth in water comprising contacting the water with a composition comprising a stable anhydrous mixture of an oxidizing agent and an active halogen agent wherein the oxidizing agent is potassium monopersulfate and the active halogen agent is an alkali metal salt of dichloro-s-triazinetrione, halogenated dimethylhydantoin, or mixtures thereof.

The present invention further comprises a method of sanitizing water comprising contacting the water with a composition comprising a stable anhydrous mixture of an oxidizing agent and an active halogen agent wherein the oxidizing agent is potassium monopersulfate and the active halogen agent is an alkali metal salt of dichloro-s-triazinetrione, halogenated dimethylhydantoin, or mixtures thereof.

DETAILED DESCRIPTION OF THE INVENTION

The present invention comprises a stable anhydrous mixture of an oxidizing and halogenating agent. The oxidizing agent is potassium monopersulfate. The term "potassium monopersulfate" is used herein to mean the triple salt $2KHSO_5 \cdot KHSO_4 \cdot K_2SO_4$, containing potassium hydrogen peroxymonosulfate, $KHSO_5$, as the active peroxygen component. Potassium monopersulfate is commercially available from E. I. du Pont de Nemours and Company, Wilmington, Del., and is sold under the trade name OXONE monopersulfate compound. The triple salt has a theoretical active oxygen content of 5.2%, although commercial products are typically about 4.7% active oxygen content. Potassium monopersulfate is a strong, but selective oxidizer useful in a wide variety of consumer and industrial applications. It is a non-chlorine oxidizer for reducing non-microbial organic contaminants in water systems without the possibility of forming irritating and malodorous chlorine disinfection byproducts associated with the use of traditional 'shock' products like sodium and calcium hypochlorite.

The term "active halogen agent" as used herein means a chemical that dissolves in water to give free available halogen. The halogen can be measured using test kits and methods well known to those skilled in the art. Depending upon the pH, the free halogen will be distributed among three molecular species: the diatomic elemental form, $X_2$, the biocidally-active hypohalous acid, HOX, and the hypohalite anion, $OX^-$ wherein X is halogen. The active halogen agent useful in the present invention is selected from active halogen agents that dissolve in water to give free chlorine or bromine, or mixtures thereof as detailed below. Optionally other additives are present in the composition of the present invention. The composition of the present invention is useful in the treatment of recirculating water systems including recreational and ornamental water treatment, and in industrial water systems such as cooling towers, evaporative condensers, and air washers. The composition of the present invention is particularly useful in swimming pool, spa, and hot tub applications. It provides the dual functions of peroxygen oxidation as well as the establishment or maintenance of a free halogen residual.

The present invention comprises blends of potassium monopersulfate and an active halogen agent that are stable and safe to handle. Potassium monopersulfate provides the benefits of peroxygen oxidation without the undesirable side-effects of high chlorine shock doses, such as the formation of irritating and malodorous chlorinated disinfection byproducts (e.g., chloramines and chloroform) which adversely impact aquatic air and water quality and reduce sanitizer efficiency. The active halogen component serves to re-establish a free halogen residual or to maintain the sanitizer level within a desired range to optimally control the growth of microorganisms and algae.

Various active halogen agents useful as sanitizing agents in recreational, ornamental and industrial waters are suitable for use in the present invention. These include the anhydrous alkali metal salts of dichloro-s-triazinetrione, particularly the sodium and potassium salts, and preferably the sodium salt. The sodium salt is also called dichloroisocyanuric acid, sodium salt. Also included are anhydrous halogenated dimethylhydantoins (dichloro, bromochloro, and dibromodimethylhydantoins). Alkali metal dichloro-s-triazinetrione has the structure of Formula 1 below wherein M denotes the alkali metal.

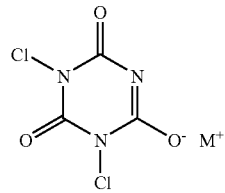

Formula 1

Sodium dichloro-s-triazinetrione is typically used in granular form as a water sanitizer. It hydrolyzes when dissolved in water to release elemental chlorine. Alkali metal dichloro-s-triazinetrione is available from Aldrich (Milwaukee Wis.) and in commercial quantities from Occidental Chemical Corporation (OxyChem, Dallas Tex.) and Shikoku Chemicals Corporation (Kagawa, Japan and Los Angeles Calif.). Sodium dichloro-s-triazinetrione is an EPA-registered santitizer in the U.S.

The active halogen agent suitable for use herein is stabilized in that the halogen is covalently bonded to nitrogen in a suitable organic molecular framework. The preferred active halogen agents (halogen sanitizers) are 1) the anhydrous alkali metal salts of dichloro-s-triazinetrione and 2) anhydrous dihalodimethylhydantoins. Anhydrous mixtures of potassium monopersulfate and anhydrous sodium dichloro-s-triazinetrione are most preferred. Suitable dry dihalodimethylhydantoins are the 1,3-dichloro-, 3-bromo-1-chloro-, or 1,3-dibromo-5,5-dimethylhydantion. Mixtures of both anhydrous alkali metal dichloro-s-triazinetrione and dihalodimethylhydantoins can also be used. The dry dihalodimethylhydantoins result in poorer flow characteristics of the mixtures without the addition of an anti-caking agent. Thus, use of an anti-caking agent such as basic precipitated magnesium carbonate, is preferred with the dihalodimethylhydantoins.

The compositions of the present invention are hereinafter expressed as the weight ratio of the potassium monopersulfate to active halogen agent, excluding other optional additives. Specifically, mixtures containing weight ratios of potassium monopersulfate to active halogen agent of from about 99:1 to about 1:99 are useful herein, wherein the former has a higher potassium monopersulfate content and the latter, a lower potassium monopersulfate content. Preferred are mixtures with weight ratios of potassium monopersulfate to active halogen agent of from about 95:5 to about 10:90, and more preferred are weight ratios from about 95:5 to about 20:80.

Different ratios are useful in the present invention for various end use applications. The blends containing higher levels of potassium monopersulfate are useful as oxidative treatments in conjunction with chlorine and bromine sanitizer systems, or combination sanitizer systems where metal ions, such as silver, copper and zinc, are used in conjunction with reduced levels of halogen sanitizers, or as "start-up" treatments at the beginning of the warm weather season. Blends containing lower levels of potassium monopersulfate are useful as sanitizing treatments for pools, spas, and hot tubs. The benefits of regular, preventative and maintenance treatments, for pools, spas, and hot tubs, with compositions of the present invention include, but are not limited to, improved water clarity, faster restoration of water quality after heavy bather load, and prevention of algae growth.

The compositions of the present invention are in the form of a solid granular mixture or a tablet. Either of these can be in pre-measured dosages wherein one or more pre-measured dosage tablets or pre-measured dosage packages of granular mixture are added to the water. Preferred is use of a solid granular mixture.

The stability of anhydrous solid mixtures of potassium monopersulfate with the active halogen agents of the present invention is unexpected. Upon storage at room temperature and in an oven at an elevated temperature of 50° C. and 80% relative humidity (the accelerated storage stability test), the compositions of the present invention remain stable and active. The compositions of the present invention maintain their granular properties, show in the worst case a mild chlorine odor, and show no signs of chemical reaction or deterioration (e.g., color formation) during such accelerated storage. Some compositions may form frangible lumps during a month's accelerated storage. Odor-absorbing compounds and anti-caking agents can be added to minimize the formation of odor and frangible lumps. However, the preferred solid mixtures of potassium monopersulfate with the active halogen compounds remain free flowing and show no more than a trace of chlorine odor. Measurement of the total active oxidant (the total oxidant measured including both active oxygen and halogen expressed as total active oxygen) after accelerated storage tests at elevated temperature demonstrated no or minimal loss of activity for the compositions of the present invention.

The solid mixtures of the present invention of potassium monopersulfate with the active halogen agents are intended to be cast into the water to be treated, that is into a large volume of water. A user, however, might misuse the mixture and mistakenly slurry the mixture in a small volume of water. For instance, the user might add the mixture to a bucket to form a slurry with a small amount of water before tossing the slurry into the large volume of water to be treated. While contrary to the recommended instructions for use, this is a foreseeable misuse. Thus, in a further evaluation of the compositions of the present invention, the solid mixture and a limited amount of water were premixed. The compositions of the present invention evolve little or no halogen under such circumstances, so as not to create a halogen gas cloud around the attendant using the mixture.

In contrast and as later shown by Comparative Example C, a blend of 80% potassium monopersulfate and 20% calcium hypochlorite becomes warm when moistened or placed in a small volume of water. This is so although the dissolution of potassium monopersulfate itself in water is endothermic. Simultaneously, chlorine gas is evolved, creating a hazard. While not wishing to be bound by theory, it is believed that chlorine gas is generated because the active chlorine in calcium hypochlorite (and other hypochlorite salts) is in the form of a very water-soluble salt and is not covalently bound to nitrogen in an organic molecule. Lacking the stabilizing effect of the organic molecular platform, the chlorine in a hypochlorite salt is immediately converted to chlorine gas in the presence of an acid source (the $KHSO_4$ component in potassium monopersulfate). Thus, mixtures of potassium monopersulfate with hypochlorite salts are not viable because they create a safety hazard due to chlorine gas generation potential and even a fire hazard in storage if product inadvertently gets wet. In the stable compositions of the present invention, the active halogen is chemically bonded to nitrogen in an organic molecule and evolution of chlorine gas is avoided.

The most preferred anhydrous mixtures of the present invention remain as free-flowing granular mixtures on storage. Mixtures of potassium monopersulfate and dihalodimethylhydantoins, while not caking, tend to form frangible agglomerates that are readily restored to free-flowing powders by shaking, stirring, or otherwise agitating the agglomerate. An additional anti-caking agent, such as magnesium carbonate, suppresses this tendency and mixtures of potassium monopersulfate and dihalodimethylhydantoins with the anti-caking agent remain as free-flowing powders. Consequently, the caking properties of the various blends are described in the following three levels, in order of decreasing acceptability: (a) free-flowing, preferred, (b) frangible, less preferred, and (c) caked (unacceptable).

A factor making the potassium monopersulfate/anhydrous sodium dichloro-s-triazinetrione blends of the present invention safe even under misuse conditions is the sharply decreased solubility of the sodium dichloro-s-triazinetrione in acidified water. The acidic $KHSO_4$ component of potassium monopersulfate decreases the pH in concentrated solutions sharply. In a 20% potassium monopersulfate solution, having a pH of about 1.2, the solubility of sodium dichloro-s-triazinetrione is depressed to about 1 g/100 mL. By comparison, its solubility in water at a neutral pH (e.g., about pH 6-7) is about 24 g/100 g $H_2O$ at 25° C. Furthermore, if a solution of sodium dichloro-s-triazinetrione in neutral water is acidified, the sodium dichloro-s-triazinetrione precipitates. The $KHSO_4$ component of potassium monopersulfate creates a very low pH in a concentrated solution. The low solubility of sodium dichloro-s-triazinetrione in water below about pH 2 is an important safety factor since this is the pH range where chlorine gas can be formed. In a 1% potassium monopersulfate solution (initial pH of 2.3), gradual addition of anhydrous sodium dichloro-s-triazinetrione slowly increases the pH, and thus gradually increases the solubility of the sodium dichloro-s-triazinetrione. Once the pH rises above about 3, which requires relatively little sodium dichloro-s-triazinetrione, the chlorine equilibrium is shifted to the HOCl form, minimizing the risk of chlorine gas formation.

Thus, a mechanism exists that limits the availability of the sodium dichloro-s-triazinetrione to form chlorine gas if the blend is misused by being dispersed in a limited volume of water. The solubility of the sodium dichloro-s-triazinetrione progressively increases with increasing pH and thus with increasing dilution. When properly dispensed into a large volume of water to be treated, the pH is essentially unchanged, and the full solubility of the sodium dichloro-s-triazinetrione is available to sanitize. Such a solubility limitation is not the case with hypochlorite salts. Other active halogen compounds included in the present invention, the dihalodimethylhydantions (dichloro-, bromochloro-, and dibromo-) also have relatively low solubility in both neutral and acidic water, and thus also do not pose a problem in the simulation of misuse. The respective solubilities in water are 0.2 g/100 g water for dichloro- and bromochlorodimethylhydantion; and 0.25 g/100 g water for dibromodimethylhydantion. Trichloro-s-triazinetrione also has limited solubility characteristics, but is not preferred due to its propensity to cake when mixed with potassium monopersulfate.

The composition of the present invention is optionally blended with other anhydrous water treatment chemicals. The types of optional additives are given below as examples and are not intended to be all-inclusive. Examples are pH buffers to help maintain balanced pH and alkalinity (e.g., anhydrous carbonates, bicarbonates, and phosphates); diluents (e.g., sodium sulfate); clarifiers (e.g., anionic, nonionic, and cationic polymers, chitin and chitosan, and aluminum salts such as sulfates); algae control agents (e.g., metal, ions such as silver, copper and zinc, quaternary ammonium chloride products such as alky dimethyl benzyl animonium chloride formulations, and polymeric quaternary aminonium chloride products); antimicrobial agents; other oxidizers (e.g., persulfates such as sodium peroxydisulfate and other peracids); halogen stabilizers (e.g., cyanuric acid, sulfamic acid, and dimethyihydantoin); miscellaneous water modifiers (e.g., chelating agents such as ethylenediamine tetraacetic acid, diethylenetriamine penteacetic acid, and citric acid); corrosion inhibitors; flocculants; anticaking agents (such as magnesium carbonate); fluorosurfactants; enzymes; biocidal polymers; lanthanum salts (such as the halides, oxycarbonates, and carboxylates), activators (such as tetreacetylethylenediamine, ketones, and the like); surfactants; fragrances; dyes; and colorants. For tablet formulations, optional additives also include excipients such as lubricants; and binders (for instance polyvinylpyrrolidone); and other tableting aids well known to those skilled in the art.

The compositions of the present invention are prepared by mixing the dry components. Mixtures of anhydrous materials are preferably prepared under humidity-controlled conditions, and packaged in sealed and moisture impermeable containers. Suitable materials for such containers are high-density poly(ethylene) and high-density poly(propylene) (HDPE and HDPP). Optionally, additives are added to the mixing step. As an example, 0 to about 20% anhydrous sodium carbonate, based on the total weight of the potassium monopersulfate-active halogen agent mixture, may be added to control pH. The materials are blended in dry equipment with ventilation and other precautions taken to prevent inhalation of dust. Use of dry equipment and anhydrous materials and storage under dry conditions is required since chlorine evolves from active halogen compounds in the presence of moisture and a source of acidity. Blending equipment may be conveniently dried by passing anhydrous sodium carbonate through the equipment to remove moisture, or by any other suitable method well known to those skilled in the art. Alternatively, the mixtures may be packaged in pre-measured amounts in water-soluble plastic pouches. Poly(vinyl alcohol) is an example of a water-soluble plastic suitable as a pouch material. Technology for such testing and pouch packaging is described in U.S. Pat. No. 6,727,219; herein incorporated by reference.

The amount of the mixture used and the ratio of potassium monopersulfate to alkali metal dichloro-s-triazinetrione or potassium monopersulfate to dihalodimethylhydantoin are based on the desired loading of the components. As a swimming pool and spa oxidative treatment, the amount of potassium monopersulfate used is determined by the volume of water to be treated and the extent of contamination (so-called "bather load"). Typical recommended potassium monopersulfate usage rates are 1-2 oz./250 gal (0.03-0.06 kg/m$^3$) for spas and 1-2 lb/10,000 gal (0.005-0.012 kg/m$^3$) for swimming pools. Typical recommended usage rates for sodium dichloro-s-triazinetrione are those doses required to establish or maintain a free available chlorine residual of 0.5-5.0 ppm (0.5-5.0 micrograms/gram) in the treated water. For uses other than treatment of recreational water, recommended usage rates are those consistent with EPA-registered label directions.

The invention provides a single, solid, and water-soluble composition, in the form of granules, tablets, or pre-measured dosage packages, which provides the dual function of peroxygen oxidation with the simultaneous establishment or maintenance of a halogen residual.

It has been found that mixtures of potassium monopersulfate with several common active halogen sources are unsuitable for various reasons. Solid alkali and alkaline earth metal hypochlorites, such as Ca(OCl)$_2$ and LiOCl, are incompatible with potassium monopersulfate due to their extreme sensitivity to moisture and low pH. Even ambient humidity suffices to generate chlorine gas and the available oxidant (chlorine and oxygen—both are measured by a total active oxidant analysis) decreases rapidly on storage. Sodium hypochlorite is only available as an aqueous solution and is also unsuitable. Furthermore, not all active halogen compounds are acceptable, e.g., the sodium and potassium dichloro-s-triazinetrione dihydrates, trichloroisocyanuric acid (trichloro-s-triazinetrione), sodium-N-chloro-p-toluenesulfonamide, and sodium N,N-dichloro-p-toluenesulfonamide are not suitable in the practice of this invention.

The present invention further comprises a method of treating water comprising adding to the water a composition comprising a stable mixture of an oxidizing agent and an active halogen agent wherein the oxidizing agent is potassium monopersulfate and the active halogen agent is an alkali metal salt of dichloro-s-triazinetrione, halogenated dimenthylhydantoin, or mixtures thereof. The method is useful for treatment of recirculating water systems including recreational, ornamental and industrial water systems, with special utility in the treatment of swimming pools, spas and hot tubs. The treatment provides both oxidizing and halogenating simultaneously and aids in controlling microbial and algal growth. Optionally, the composition used in the method of the present invention may contain other additives, such as a buffer for pH adjustment, a clarifying agent, etc., as listed above. Specifically, these compositions are useful as oxidative treatments in combination with sanitizer systems where metal ions are used in conjunction with reduced levels of halogen sanitizers. The blends are also useful as "start-up" treatments at the beginning of the warm weather season, as end-of-season winterizing oxidative treatments, and as regular, maintenance doses for swimming pools, spas, and hot tubs.

The present invention further comprises a method to inhibit algae growth in water comprising contacting the water with a composition comprising a stable anhydrous mixture of an oxidizing agent and an active halogen agent wherein the oxidizing agent is potassium monopersulfate and the active halogen agent is an alkali metal salt of dichloro-s-triazinetrione, halogenated dimethylhydantoin, or mixtures thereof. This method is useful for treatment of recirculating water systems such as recreational, ornamental and industrial water systems. The method is useful to inhibit algae growth or to provide algicidal activity. The composition used in this method can contain other additives as detailed above. The stable composition used in this method permits easy convenient treatment of water to control algae.

The present invention further comprises a method of sanitizing water comprising contacting the water with a composition comprising a stable anhydrous mixture of an oxidizing agent and an active halogen agent wherein the oxidizing agent is potassium monopersulfate and the active halogen agent is an alkali metal salt of dichloro-s-triazinetrione, halogenated dimethylhydantoin, or mixtures thereof. This method is useful for treatment of recirculating water systems such as recreational, ornamental and industrial water systems. The method is useful to inhibit microbial and algae/algal growth in the water. The compositions of the present invention provide both antibacterial and algicidal efficacy to treated water. The composition used in this method can contain other additives as detailed above. The stable composition permits easy convenient treatment of water to sanitize.

Materials and Test Methods

OXONE monopersulfate compound is available from E. I. du Pont de Nemours and Company, Wilmington Del.

Anhydrous sodium dichloro-s-triazinetrione is available from Aldrich (Milwaukee Wis.). Commercial quantities are available from Occidental Chemical Corporation (OxyChem, Dallas Tex.) and Shikoku Chemicals Corporation (Kagawa, Japan and Los Angeles Calif.).

1,3-dichloro-5,5-dimethylhydantoin is available from Alfa Aesar (Ward Hill Mass.)

3-bromo-1-chloro-5,5-dimethylhydantoin is available from Aldrich (Milwaukee Wis.)

1,3-dibromo-5,5-dimethylhydantoin is available from Acros Chemicals (Morris Plains N.J.)

Test Method 1. Active Oxidant Measurement

In all examples, active oxidant concentrations are expressed in weight percent and are determined by standard iodometric titration as described in the "OXONE Monopersulfate Compound Technical Information" Bulletin, No. H-42434-5, dated April 2000, published by E. I. du Pont de Nemours and Company.

A weighed sample (0.05-0.30 g) to be analyzed is dissolved in cold deionized water (<10° C., about 50 mL), treated with potassium iodide solution (10 mL 25% aqueous), acidified (10 mL 20% sulfuric acid), and titrated with standardized 0.1N sodium thiosulfate reagent to an endpoint visualized by a starch indicator. The total active oxidant content (active oxygen+active halogen) is expressed as percent active oxygen (% AO) and is calculated as follows:

% $AO$=(0.8×Volume of titrant, mL)(Normality of titrant)/(Sample Weight, g).

The halogen-generating component of the compositions of the present invention (e.g., anhydrous dichloro-s-triazinetrione) ranges from about 1-99% by weight of the blend (potassium monopersulfate:active halogen agent ratios of from about 99:1 to about 1:99). Despite the low percentage of the active halogen component in some of the compositions, its contribution to total active oxidant is readily measured by this method since its contribution is disproportionate to the composition ratio. Table 1 below illustrates this point for the case of hypothetical blends containing only OXONE and anhydrous sodium dichloro-s-triazinetrione in the ratios of the present invention. Thus, any decay occurring in either the active oxygen (AO) or active chlorine (AC) components would be readily detected as a reduction in assay of total active oxidant. Table 1 provides the contributions of active oxygen (AO) and active chlorine (AC) to total active oxidant for selected blends on OXONE brand potassium monopersulfate and anhydrous sodium dichloro-s-triazinetrione (ASDC).

TABLE 1

| | OXONE/ASDC Ratio | | | | | | | |
|---|---|---|---|---|---|---|---|---|
| | 99:1 | 95:5 | 90:10 | 60:40 | 40:60 | 20:80 | 10:90 | 1:99 |
| Wt. % OXONE | 99 | 95 | 90 | 60 | 40 | 20 | 10 | 1 |
| Wt. % ASDC | 1 | 5 | 10 | 40 | 60 | 80 | 90 | 99 |
| % AO from OXONE (1) | 4.65 | 4.47 | 4.23 | 2.82 | 1.88 | 0.94 | 0.47 | 0.05 |
| % AC from ASDC (2) | 0.63 | 3.13 | 6.25 | 25.00 | 37.50 | 50.00 | 56.25 | 61.88 |
| Equivalent % AO from ASDC (3) | 0.14 | 0.71 | 1.41 | 5.64 | 8.46 | 11.28 | 12.69 | 13.96 |
| Total Oxidizer as % AO (4) | 4.79 | 5.17 | 5.64 | 8.46 | 10.34 | 12.22 | 13.16 | 14.01 |

TABLE 1-continued

| | OXONE/ASDC Ratio | | | | | | | |
|---|---|---|---|---|---|---|---|---|
| | 99:1 | 95:5 | 90:10 | 60:40 | 40:60 | 20:80 | 10:90 | 1:99 |
| % Total AO from ASDC (5) | 2.94 | 13.64 | 25.01 | 66.67 | 81.82 | 92.31 | 96.43 | 99.66 |

(1) Assumes 100% OXONE has 4.70% AO.
(2) Assumes the AC of 100% anhydrous sodium dichloro-s-triazinetrione is 62.5%.
(3) Conversion factor from AC to AO is the ratio of the atomic weight of O to the molecular weight of $Cl_2$, (16/70.9 = 0.226).
(4) Sum of "% AO from OXONE" and "Equivalent % AO from ASDC".
(5) 100 × ("Equivalent % AO from ASDC")/("Total Oxidizer as % AO").

Test Method 2. Accelerated Rate Calorimetry (ARC).

ARC measurements were made on equipment manufactured by Tiax Corporation of Boston, Mass. as a measure of thermal stability of the compositions. The equipment was used in accordance with manufacturer's recommendations.

A sample was charged into a 10-mL stainless steel, HASTELLOY, or titanium bomb. The bomb was immersed in a furnace surrounded by a thick shell capable of withstanding pressures up to 20,000 psi (138 Mpa). A thermocouple clipped to outside of the bomb indicated the sample temperature. The bomb was heated by a radiant heater and the output of the thermocouple was used to control the temperature in the furnace. A pressure transducer measured the pressure in the system.

A typical test consisted of heat, wait and search modes. The bomb is heated at 1° C./min up to a predetermined temperature, where the temperature was maintained for 10 minutes. During this wait time, any exothermic activity caused the sample temperature to rise. If a rate of temperature rise of 0.02° C./min was observed, the temperature control in the system was switched to adiabatic mode, i.e., the surrounding furnace temperature was kept at the sample temperature. Under adiabatic conditions, the heat loss from the bomb is minimal and the heat of reaction was used to heat the sample and the bomb only. If no exothermic activity was detected, the bomb was heated by 10° C. and the wait and search mode starts again.

The minimum temperature at which exothermic behavior is observed is the "onset temperature". A sample must be stored below the onset temperature. The ARC system has high thermal inertia, defined as:

$T_{inertia}=1+(m_b C_{pb}/m_s C_{ps})$ wherein
 $m_b$ is mass of the bomb,
 $C_{pb}$ is heat capacity of the bomb,
 $m_s$ is the mass of the sample, and
 $C_{ps}$ is the heat capacity of the sample
 The $T_{inertia}$ factor of an ARC bomb varies between 1.5 and 6.0 depending on material of construction of the bomb. ARC results should not be extrapolated for actual situations without applying phi correction since in actual situations the phi factor is close to 1.

Test Methods 3 and 4.

The Test Methods used to demonstrate the antibacterial and algicidal properties of the compositions of the present invention are described in Examples 17-24 and 25-28, respectively.

EXAMPLES

The following examples are presented to demonstrate the invention, but are not intended to be limiting.

Example 1

OXONE monopersulfate compound (180 g, 90 wt. %) and anhydrous sodium dichloro-s-triazinetrione (20 g, 10 wt. %) were dry blended in a 250-ml high-density poly(propylene) (HDPE) bottle. The mixture was placed on a laboratory roll mill for two hours to ensure complete blending of the components. The blended product was then divided into two portions. One portion was stored at ambient conditions (22+/−2° C., 55+/−5% relative humidity [RH]); the other in a humid oven at 50+/−2° C., 80+/−5% RH denoted as "accelerated aging"). Both portions were stored in sealed screw-cap HDPE bottles. Both samples were monitored on a weekly basis for one month to assess physical integrity and active oxidant loss. The sample at ambient storage conditions remained free flowing, showed no loss in active oxidant concentration, and served as a control. The results for the 'humid' oven sample are shown in Table 2 below. It can be seen that even under accelerated aging, the blend remained free flowing, and exhibited minimal chlorine odor and active oxidant loss after one month.

Examples 2-12, Comparative Examples A-E

Examples 2-12 and Comparative Examples A-E were prepared as described in Example 1 with the component proportions in weight percent as listed in Table 2. As in Example 1, all of the samples at ambient temperature and relative humidity remained free flowing, showed excellent active oxidant stability, and served as control samples. The results for the corresponding accelerated aging storage samples are given in Table 2. It can be seen that Examples 2-12 showed excellent flow properties, low odor, and excellent active oxidant retention after one month at high temperature and 80% relative humidity.

Comparative Examples A-C, having the compositions defined in Table 2, became caked, exhibited dangerous and malodorous chlorine gas generation, and showed significant loss in active oxidant content. Control C was so unstable from the standpoint of chlorine gas generation that it could not be stored safely at 50° C. for more than a few days. Comparative Example D was a 100% OXONE control. It exhibited good flowability, very low odor, and excellent active oxidant stability after one month accelerated aging. Comparative Example E was a 100% anhydrous sodium dichloro-s-triazinetrione control. It exhibited good flowability, a characteristic chlorine odor, and acceptable active oxidant stability after one month accelerated aging.

TABLE 2

| Ex. # (1) | Composition, wt %, abbreviations below. | Flowability | Chlorine Odor (3) | Total % AO Remaining (%) (2) |
|---|---|---|---|---|
| EXAMPLES | | | | |
| 1 | 90/10 OXONE/ASDC (6) | Free-flowing | 1 | 100 |
| 2 | 80/20 OXONE/ASDC | Free-flowing | 2 | 97 |
| 3 | 70/30 OXONE/ASDC | Free-flowing | 2 | 97 |
| 4 | 60/40 OXONE/ASDC | Free-flowing | 3 | 100 |
| 5 | 40/60 OXONE/ASDC | Free-flowing | 3 | 100 |
| 6 | 20/80 OXONE/ASDC | Free-flowing | 3 | 100 |
| 7 | 95/5 OXONE/ASDC | Frangible | 1 | 87 |
| 8 | 97.5/2.5 OXONE/ASDC | Frangible | 0.5 | 80 |
| 9 | 80/10/10 OXONE/ASDC/Na$_2$CO$_3$ | Free-flowing | 0 | 96 |
| 10 | 80/20 OXONE/BCDMH | Frangible | 1 | 98 |
| 11 | 80/20 OXONE/DBDMH | Frangible | 1 | 100 |
| 12 | 80/20 OXONE/DCDMH | Frangible | 2 | 99 |
| COMPARATIVE EXAMPLES | | | | |
| A | 80/20 OXONE/SDCDH | Caked | 5 (4) | 29 |
| B | 80/20 OXONE/TC | Caked | 5 | 69 |
| C | 80/20 OXONE/CaH | Caked | 5 (4) | Unstable |
| D | 100 OXONE (Control) | Frangible | 0 | 96 |
| E | 100 ASDC (Control) | Free-flowing | 3 | 93 |

(1) Examples denoted by numerals, Comparative Examples and Controls by letters.
(2) Samples tested in sealed, screw-cap high-density polyethylene containers.
(3) Degree of chlorine odor: 0 = no odor, 5 = strong odor, indicating chlorine evolution during the accelerated storage test.
(4) Visible chlorine gas evolution with pressure build-up
(5) Total percent oxidant content (= active oxygen + active halogen) remaining after the accelerated storage test.
(6) Composition Abbreviations:
ASDC: Anhydrous sodium dichloro-s-triazinetrione.
Na$_2$CO$_3$: anhydrous sodium carbonate.
BCDMH: 3-bromo-1-chloro-5,5-dimethylhydantoin.
DBDMH: 1,3-dibromo-5,5-dimethylhydantoin.
DCDMH: 1,3-dichloro-5,5-dimethylhydantoin.
SDCDH: sodium dichloro-s-triazinetrione dihydrate.
TC: trichloro-s-triazinetrione.
CaH: calcium hypochlorite.

The data in Table 2 show that, under accelerated aging storage conditions, the compositions of the invention provided desirable storage stability and minimal halogen evolution. Additionally, they showed good retention of the total active oxidant (the combination of active oxygen and active halogen). Comparative Examples A, B and C were not stable upon storage under these conditions.

Examples 13 and 14, Comparative Examples C. C', D, and D'

Example 13 and Comparative Examples C and D were prepared as described in Example 1 with the component proportions listed in Table 3. The thermal stabilities of these Examples were determined using accelerated rate calorimetry (ARC, see test Method above). These data are presented in Table 3 for three dry samples (13, C, and D) and three corresponding samples where 3 percent by weight water, based on the weight of the dry sample, was added to the sample prior to heating (14, C', and D'). In this method, the sample was slowly heated under adiabatic conditions through the temperature range in which the sample shows exothermic properties. In Table 3, "$T_{initial}$" represents the temperature at which self-heating begins. The "Max SHR" represents the maximum self-heat rate. This is the maximum slope achieved in the temperature versus time data plot. Finally, "Total Heat" is the total heat evolved as a result of thermal decomposition, i.e., a measure of the total exotherm. Stable compositions were characterized by relatively high $T_{initial}$, low Max SHR values, and low Total Heat values versus a suitable control standard such as OXONE, a long-standing and safe commercial product.

The data in Table 3 show that blends of OXONE and anhydrous sodium dichloro-s-triazinetrione (Example 13, dry, and 14, wet) had very similar thermal stability characteristics to that of OXONE itself, both dry (Comparative Example D) and wet (Comparative Example D'). In contrast, it can be seen that blends of OXONE and calcium hypochlorite (Comparative Example C, dry, and C', wet) were thermally unstable. This was evidenced by the high self-heating rate for the dry sample C and the very low onset temperature for the wet sample C'.

TABLE 3

| Ex. # | Composition*, wt % | $T_{Initial}$* (° C.) | Max. SHR* (° C./min) | Total Heat* (Cal/g) |
|---|---|---|---|---|
| EXAMPLES | | | | |
| 13 | 86/14 OXONE/ASDC | 105 | 1.0 | 55 |
| 14 | 86/14 OXONE/ASDC + 3% water | 80 | 0.5 | 47 |
| COMPARATIVE EXAMPLES | | | | |
| D | 100 OXONE | 100 | 5.1 | 70 |
| D' | 100 OXONE + 3% water | 80 | 0.3 | 72 |
| C | 86/14 OXONE/CH | 131 | 67.7 | 34 |
| C' | 86/14 OXONE/CH + 3% water | 29 | 7.2 | 68 |

*Component abbreviations as for Table 2, $T_{Initial}$, Max. SHR, and Total Heat: see above.

Example 15

Synthetic pool water (1200+/−50 liters) was prepared by balancing pH (7.5+/−0.1, using aqueous hydrochloric acid), alkalinity (120+/−10 ppm, as $CaCO_3$, using sodium bicarbonate), calcium hardness (220 ppm, as $CaCO_3$, using calcium chloride dihydrate), and initial active chlorine (1.1 ppm free chlorine, using 5% liquid sodium hypochlorite). Alkalinity and calcium hardness were measured using a Lamotte Pro 250 DPD Test Kit (Lamotte Co., Chestertown, Md.) according to the manufacturer's directions. Free chlorine was measured titrimetrically using Method #4500Cl-S (ferrous ammonium sulfate) as described in "Standard Methods for the Examination of Water and Wastewater", 19$^{th}$ edition, American Public Health Association, Washington, D.C., 1995. A blend containing 80 wt. % OXONE and 20 wt. % anhydrous sodium dichloro-s-triazinetrione was prepared as described in Example 1. A 30-gram dose (25 ppm) of the granular mixture was broadcast into the recirculating synthetic pool water equilibrated to 28+/−2° C. One hour after sample addition, the pool water was again analyzed for free chlorine and active oxygen using the modification of Method 4500Cl-S described in Kroll, U.S. Pat. No. 6,180,412, to eliminate monopersulfate interference in active chlorine measurements. The free chlorine was found to have increased by 2.8 ppm (90% of theoretical) and an active oxygen residual of 0.77 ppm (16.4 ppm OXONE, 82% of theoretical). The residual values for active chlorine and active oxygen were somewhat less than 100% because of uncertainty in the total water volume and oxidative demand of the water. Treatment of a large volume of synthetic pool water with an OXONE/anhydrous sodium dichloro-s-triazinetrione blend of the present invention resulted in a measured increase in both residual active oxygen and active chlorine concentrations.

Example 16

A granular mixture (200 g) was prepared by blending 140 g OXONE, 20 g anhydrous sodium dichloro-s-triazinetrione, 20 g anhydrous sodium carbonate, and 20 g boric acid as a tablet release agent. The mixture was rolled on a laboratory roll mill for one hour to ensure uniform blending of the components. Thirty-gram cylindrical tablets were formed using a Carver press (Fred S. Carver, Inc., Menomonee Falls, Wis.; 29 mm die, 3000 psi, 1 second dwell time). The tablets were well formed with excellent physical integrity.

To simulate a pool application, a tote tank equipped with a sand-filtered circulation system, was fully charged with tap water (1200 L equilibrated to 28-30° C.). The filtration rate was 2.4 L/s giving a turnover rate of 8.3 minutes. The tap water was conditioned as follows:

1) for alkalinity using sodium bicarbonate to the desired level of 100-120 mg/L calcium carbonate,
2) for hardness using calcium chloride to 240 to 260 mg/L calcium carbonate,
3) for residual chlorine using sodium hypochlorite to a level of 1.2 mg/L free available chlorine (FAC), expressed as Cl2, and finally
4) to a pH of 7.50 using 18% aqueous hydrochloric acid.

One tablet was added to the conditioned water and it dissolved rapidly (within 2 minutes). After 30 minutes, the water was re-analyzed as follows, with the calculated or expected values shown in parentheses:

OXONE=15 mg/L (17.5 mg/L)
FAC=2.8 mg/L, an increase of 2.8−1.2=1.6 mg/L (increase 1.56 mg/L)
pH=7.47 (7.5)
Alkalinity=110 mg/L (100 to 120 mg/L)
Calcium hardness=260 mg/L (240 to 260 mg/L)

Thus it can be seen that dosing the recirculating water with a tableted composition of the present invention resulted in the establishment of an OXONE residual, an increase in the free available chlorine residual by 1.6 mg/L, without a significant impact on pH, alkalinity and hardness.

Examples 17-24

Examples 17-24 demonstrate the bacterial efficacy of two representative compositions of the present invention against *E. Coli* (ATCC 11229) and *Enterococcus faecium* (ATCC 6569). The efficacy tests were conducted using a modified version of the AOAC Official Method 965.13, "Disinfectants for swimming pools". The only modification was that the centrifugation and the corresponding rinse of the microbial suspension were not performed. The compositions tested consisted of the following: an 80/20 weight percent blend of OXONE and anhydrous sodium dichloro-s-triazinetrione (Examples 17-20) and a 70/30 weight percent blend of OXONE and 3-bromo-1-chloro-5,5-dimethylhydantoin (Examples 21-24). These blends were prepared as described in Example 1 using the weight proportions described above. For each composition, nominal solution concentrations of 3, 6, 12 and 24 mg/L were used to challenge each organism. Appropriate dilutions were made from 24 mg/L buffered (0.01125 M KH2PO4, pH 7.5) stock solutions of each test composition. The solutions were tested for free chlorine based on the standard method 4500-Cl F. DPD Ferrous Titrimetric from the 19th edition (1995) of the Standard Methods for the Examination of Water and Wastewater.

The *E. coli* (ATCC 11229) and *Enterococcus faecium* (ATCC 6569) innocula were prepared by transferring each culture on Trypticase Soy Agar (TSA) [BD Biosciences, Sparks, Md.] four times. The suspension was made by adding 5 mL of sterile Butterfield buffer [BD Biosciences, Sparks, Md.] to a plate and then dispersing the colonies using a sterile L-shaped rod. The suspension was then moved from the plate to a sterile Nephelometer flask. Next, 2 mL of Butterfield buffer were added to the original plate, swirled, and also added to the Nephelometer flask. Using a Klett Colorimeter, an initial Klett reading was taken and the suspension was diluted with Butterfield buffer to reach a Klett reading of approximately 50, which is equivalent to 1.0 E+08 CFU/mL ($10^8$). A Klett reading is a measure of optical density on a calorimeter, which correlates to cell density.

The test solutions were prepared using 1 mL of innoculum added to 200 mL of disinfectant solution in a 500 mL flask, with stirring. After 30 seconds, a serial dilution plate count was performed on TSA and neutralized with D/E Neutralizing Broth/Agar (available from BD Biosciences, Sparks, Md.) at a 10:1 dilution. A representative composition of the neutralizing broth/agar is:

| | | | |
|---|---|---|---|
| Yeast Extract: | 2.5 g/L | Dextrose: | 10.0 g/L |
| Casein Digest Peptone: | 5.0 g/L | Lecithin: | 7.0 g/L |
| Sodium thioglycolate: | 1.0 g/L | Sodium thiosulfate: | 6.0 g/L |
| Sodium bisulfite: | 2.5 g/L | Polysorbate 80: | 5.0 g/L |
| Bromocresol purple: | 0.02 g/L | Agar: | 15.0 g/L |

In addition to the test solutions, an innoculum test control was conducted in the same manner as the test solutions.

The results are summarized in Table 4.

TABLE 4*

| Ex. # | Composition, wt % | Dose (mg/L) | E. coli (1) CFU/mL (3) | Delta t (4) | Enterococcus faecium (2) CFU/ml (3) | Delta t (4) |
|---|---|---|---|---|---|---|
| 17 | 80/20 OXONE/ ASDC | 3 | <1.0E+01 | 5.2 | 5.40E+05 | −0.2 |
| 18 | 80/20 OXONE/ ASDC | 6 | <1.0E+01 | 5.2 | 8.50E+01 | 3.6 |
| 19 | 80/20 OXONE/ ASDC | 12 | <1.0E+01 | 5.2 | <1.0E+01 | 4.5 |
| 20 | 80/20 OXONE/ ASDC | 24 | <1.0E+01 | 5.2 | <1.0E+01 | 4.5 |
| 21 | 70/30 OXONE/ BCDMH | 3 | 6.35E+03 | 2.4 | 3.95E+05 | −0.1 |
| 22 | 70/30 OXONE/ BCDMH | 6 | <1.0E+01 | 5.2 | 5.60E+05 | −0.2 |
| 23 | 70/30 OXONE/ BCDMH | 12 | <1.0E+01 | 5.2 | 2.75E+05 | −0.1 |
| 24 | 70/30 OXONE/ BCDMH | 24 | <1.0E+01 | 5.2 | <1.0E+01 | 4.5 |

*The notation used in quantifying CFU/mL in the format 5.40E+05 indicates $5.40 \times 10^5$.
(1) Inoculum was 1.63E+06 CFU/mL.
(2) Inoculum was 3.30E+05 CFU/mL.
(3) Lower detection limit was <1.0E+11 CFU/mL.
(4) Delta t = log $(CFU/mL)_{control}$ − log $(CFU/mL)_{test}$, where $(CFU/mL)_{control}$ is the cell concentration for the control innoculum and $(CFU/mL)_{test}$ is the cell concentration for the test innoculum.

Larger Delta t values indicate a higher level of kill. A delta t value of greater than 3.0 signifies greater than 99.9% reduction, a delta t value of greater than 5.0 represents greater than 99.999 reduction. The accepted standard for sanitization is a delta t of 3.0 in 30 s, and for disinfection a delta t of 5.0 in 10 min. Delta t values, however, are arithmetically limited to a maximum value based on the CFU/mL value for the initial inoculum. Based on the initial inoculum of *Enterococcus faecium*, a delta t value of 4.5 is the maximum achievable.

Table 4 shows that each blend was efficacious against both *E. coli* and *Enterococcus faecium*. The OXONE/anhydrous sodium dichloro-s-triazinetrione blend provided a Delta t greater than 5 at greater than or equal to 3 mg/L against *E. coli* and a Delta t greater than 3 at greater than or equal to 6 mg/L for *Enterococcus faecium*. The OXONE/3-bromo-1-chloro-5,5-dimethyhydantoin blend demonstrated a Delta t greater than 5 against *E. coli* at greater than or equal to 6 mg/L and a Delta t greater than 4 against *Enterococcus faecium* at 24 mg/L.

Examples 25-28

Examples 25-28 illustrate the effect of two compositions of the present invention on the growth of a blue-green alga, *Anabaena flos-aquae,* and a green alga, *Selenastrum capricornutum.*

The test compositions used for these tests were an 80/20 weight percent blend of OXONE and anhydrous sodium dichloro-s-triazinetrione and a 70/30 weight percent blend of OXONE and 3-bromo-1-chloro-5,5-dimethyhydantoin, as described in Examples 17-24. For each composition, nominal concentrations of 1.5, 3.0, 6.0, 12.0 and 24.0 mg/L were used to challenge each alga type.

Definitive growth inhibition studies were carried out using the OECD (Organization for Economic Cooperation and Development) Guideline Method No. 201, "Algal Growth Inhibition Test", with the following procedural modifications:

1. A 'no effect' low concentration was not determined; rather, the lowest nominal concentration tested for each test composition was 1.5 mg/L.
2. Direct counting of cells was not done every 24 hours; rather, it was done at the conclusion of each growth inhibition test (after 72 hours for *Selenastrum capricornutum* and 96 hours for *Anabaena flos-aquae).*
3. Two replicates were done instead of 3-6 replicates for controls and each test concentration.
4. The degree of growth inhibition was based solely upon healthy cell count measurements.
5. Nominal concentrations of the test compositions were used and analyses for active components in test solutions were not performed.

Briefly, the studies were performed in sterile glassware using both viability and sterility controls. An algal suspension of known cell concentration was added to flasks containing the appropriate concentrations of the test composition, and the flasks were continuously shaken and incubated for 72 hours for *Selenastrum capricornutum* and 96 hours for *Anabaena flos-aquae* under continuous fluorescent light at a temperature of 25±1° C. In all experiments, the pH was maintained in the range 6.8 to 7.9. At the conclusion of the total exposure time, healthy cell counts were determined by visual counting.

As a further test for algicidal activity, the ability of the organisms to recover after 7 days was assessed for each definitive test concentration with 50% or greater growth inhibition. The environmental conditions described above for the definitive tests apply for the recovery tests. The results for the definitive and 7-day recovery tests are given in Table 5.

TABLE 5

| Ex. # | Test Composition (3) | Algae Type | $EC_{50}$, mg/L (1) | Minimum Algicidal Concentration, mg/L (2) |
|---|---|---|---|---|
| 25 | 80/20 OXONE/ ASDC | *Anabaena flosaquae* | <1.5 | 1.5 |
| 26 | 80/20 OXONE/ ASDC | *Selenastrum capricornutum* | <1.5 | 1.5 |
| 27 | 70/30 OXONE/ BCDMH | *Anabaena flosaquae* | <1.5 | 3.0 |
| 28 | 70/30 OXONE/ BCDMH | *Selenastrum capricornutum* | <1.5 | 12.0 |

(1) $EC_{50}$ is the concentration of the test composition resulting in 50% growth inhibition.
(2) Minimum algicidal concentration is the concentration of the test composition which results in no cell re-growth in the 7-day recovery test.
(3) ASDC is anhydrous sodium dichloro-5-triazinetrione, BCDMH is 3-bromo-1-chloro-5,5-dimethyhydantoin.

The results in Table 4 indicate that compositions of the present invention very effectively inhibit the growth of *Anabaena flos-aquae* and *Selenastrum capricornutum* at dose concentrations at or below 1.5 mg/L. Further, the compositions are algicidal at or below typical use concentrations.

What is claimed is:

1. A composition consisting of a free flowing granular anhydrous mixture of an oxidizing agent; an active halogen agent for treating recirculating water systems, which is stable for at least one month a pH buffer and a clarifying agent; wherein the oxidizing agent is the triple salt $2KHSO_5 \cdot KHSO_4 \cdot K_2SO_4$ and the active halogen agent is anhydrous sodium dichloro-s-triazinetrione, and wherein the weight ratio of oxidizing agent to active halogen agent is from about 99:1 to about 70:30, and wherein a solution of said mixture in water has a pH of about 6.8 to about 7.9.

2. A method of treating water comprising contacting the water with the composition of claim.

3. A method to inhibit algae growth in water comprising contacting the water with the composition of claim 1 wherein the oxidizing agent is potassium monopersulfate and the active halogen agent is an alkali metal salt of dichloro-s-triazinetrione, halogenated dimethylhydantoin or mixtures thereof.

4. A method of sanitizing water comprising contacting the water with the composition of claim 1 wherein the oxidizing agent is potassium monopersulfate and the active halogen agent is an alkali metal salt of dichloro-s-triazinetrione, halogenated dimethylhydantoin or mixtures thereof.

5. The method of claim 2 or 3 wherein the water is a recreational, ornamental, or industrial water system.

6. The method of claim 2 or 3 wherein the treating comprises oxidizing and halogenating.

* * * * *